United States Patent [19]

Chervitz et al.

[11] Patent Number: 5,645,568

[45] Date of Patent: Jul. 8, 1997

[54] EXPANDABLE BODY SUTURE

[75] Inventors: Alan Chervitz; Ramarao Gundlapalli, both of Logan, Utah

[73] Assignee: MedicineLodge, Inc., Logan, Utah

[21] Appl. No.: 560,682

[22] Filed: Nov. 20, 1995

[51] Int. Cl.⁶ .................................................. A61B 17/04
[52] U.S. Cl. ............................................................. 606/228
[58] Field of Search ................................... 606/228, 151, 606/232

[56] References Cited

U.S. PATENT DOCUMENTS

| | | |
|---|---|---|
| 3,991,512 | 11/1976 | Stanzel . |
| 4,122,129 | 10/1978 | Casey et al. . |
| 4,549,545 | 10/1985 | Levy . |
| 4,635,637 | 1/1987 | Schreiber . |
| 4,649,920 | 3/1987 | Rhum . |
| 4,712,550 | 12/1987 | Sinnett . |
| 4,741,330 | 5/1988 | Hayhurst . |
| 4,781,190 | 11/1988 | Lee . |
| 4,788,979 | 12/1988 | Jarrett et al. . |
| 4,790,303 | 12/1988 | Steffee . |
| 4,858,603 | 8/1989 | Clemow et al. . |
| 4,869,242 | 9/1989 | Galluzzo . |
| 4,873,976 | 10/1989 | Schreiber . |
| 4,875,479 | 10/1989 | Belykh et al. . |
| 4,895,148 | 1/1990 | Bays et al. . |
| 4,926,860 | 5/1990 | Stice et al. . |
| 4,950,285 | 8/1990 | Wilk . |
| 4,976,715 | 12/1990 | Bays et al. . |
| 4,981,149 | 1/1991 | Yoon et al. . |
| 4,997,436 | 3/1991 | Oberlander . |
| 5,002,562 | 3/1991 | Oberlander . |
| 5,053,047 | 10/1991 | Yoon . |
| 5,059,206 | 10/1991 | Winters . |
| 5,076,807 | 12/1991 | Bezwada et al. . |
| 5,102,421 | 4/1992 | Anspach, Jr. . |
| 5,154,189 | 10/1992 | Oberlander . |
| 5,219,359 | 6/1993 | McQuilkin et al. ................ 606/232 |
| 5,366,480 | 11/1994 | Corriveau et al. ................ 606/233 |
| 5,374,268 | 12/1994 | Sander . |
| 5,383,904 | 1/1995 | Totakura et al. . |
| 5,450,860 | 9/1995 | O'Connor ........................ 128/898 |

*Primary Examiner*—Michael Buiz
*Assistant Examiner*—Tina T. D. Pham
*Attorney, Agent, or Firm*—M. Reid Russell

[57] ABSTRACT

An expandable body suture that has a suture body that is formed in the manufacturing process over at least one pledget device that has an elongate shape with essentially a constant cross section along its mid-section and is of a diameter to fit snugly into a hole formed in a bone, ligament, tendon, or the like. The pledget device can be formed from a cloth, fabric or resinous material, is preferably resilient, is positioned in the suture body during manufacture or can be arranged on a cord or string whereover the suture body is formed during its manufacture as by weaving suture threads or strands thereover. For forming a hole in bone, ligament or tendon to receive the pledget device pulled therein, a needle or needles are secured to the suture body end or ends for forming the hole and pulling the suture body therethrough.

12 Claims, 2 Drawing Sheets

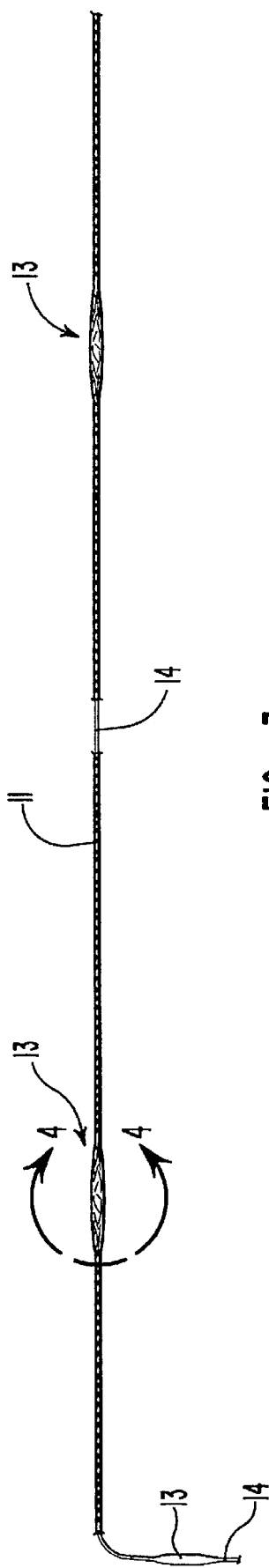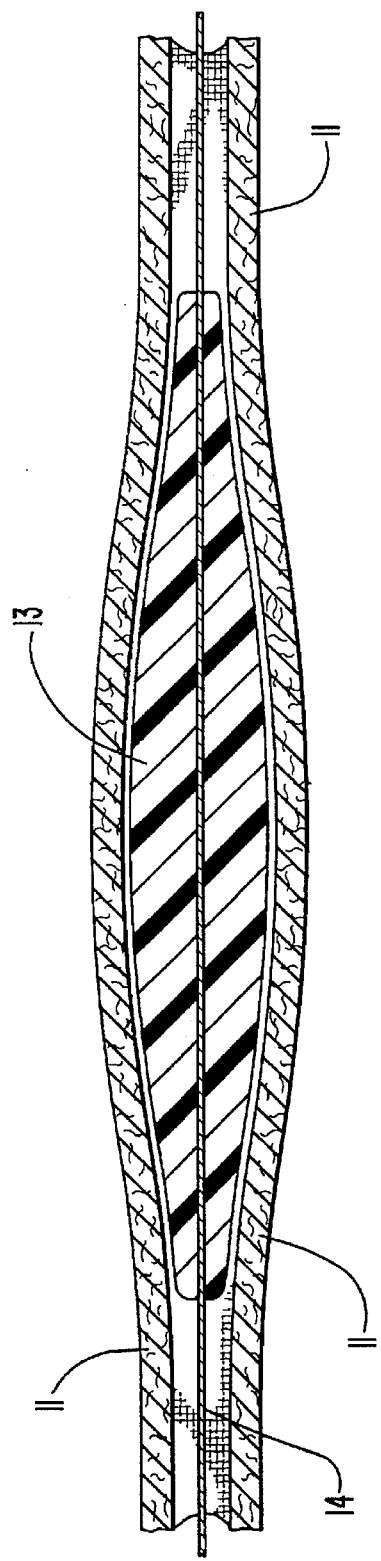
FIG. 3
FIG. 4

EXPANDABLE BODY SUTURE

BACKGROUND OF THE INVENTION

1. Field of the Invention

This invention relates to sutures, and in particular to sutures that include at least one pledget formed therewith of a size to fit snugly in a hole formed into a bone, ligament, or the like.

2. Prior Art

In a surgical procedure for passing a suture into a bone, tendon, ligament, or the like, a hole is generally formed by a needle, or the like, to fit the suture into. Often, to form such hole, a needle, that may be curved or straight, is secured onto the suture end, the suture to follow the needle through the formed hole. Accordingly, as the diameter of the suture and needle junction is greater than the suture diameter, the suture will loosely fit in the hole. Where the suture is under stress, as when it is used to tie a ligament, or the like, onto the bone surface at the hole, the loose fitting suture may move within the hole to become frayed, possibly causing it to fail. The present invention, provides for the inclusion of a pledget, enlarged area, bump, or the like, that is formed in the suture body, that, when that pledget is fitted into the formed hole, provides a tight fit in a hole, resisting damage when a force is applied to the suture, providing for a lower load per unit area on the suture area within the formed hole.

A formation of a enlarged section, pledget, or the like, onto a suture that includes needles connected onto suture ends is not new, and examples of such are shown in U.S. Pat. Nos. 4,549,545; 4,981,149; 5,374,268 and 5,383,904. All of which patents show a suture whereon has been secured a raised section, pledget, or the like, that are distinct from the present invention that provides for forming a suture with a pledget type device therein.

SUMMARY OF THE INVENTION

It is a principal object of the present invention in an expanded body suture to provide a suture body wherein one or more pledgets or enlarged sections are formed in the manufacture thereof.

Another object of the present invention is to provide a suture body that is formed around and along a string whereon one or more spaced pledgets or enlarged sections are formed, providing a suture body that contains the spaced pledgets or sections.

Another object of the present invention is to provide a suture body whereto a needle or needles are connected to the suture body ends and including one or more pledgets or enlarged sections formed at spaced intervals within the suture body, a pledget or enlarged section to fit snugly within a hole formed by a needle.

Still another object of the present invention is to provide a suture that contains one or more pledgets, enlarged sections or the like that each have a round, elliptical, square, triangular, or like, cross section and are of an appropriate length to fit into a hole or passage formed in a bone, ligament, or the like.

In accordance with the above objects, the principal features of the expanded body suture include forming, as by braiding, or the like, the suture material around to contain one or more pledgets, enlarged sections, or the like, arranged at spaced intervals therealong. The pledgets or enlarged sections to each have essentially a uniform diameter therealong and may be formed to have a round, elliptical, square, or other desired cross section, of essentially the same cross sectional area as the coupling of a suture end and the end of a needle that is used to form a hole or passage in a bone, ligament, or the like, that the suture is passed into. The suture internal pledget, enlarged section, of the like to fit snugly in the formed hole or passage.

Preferably, in the manufacture of the invention, a string with one or more pledgets formed at spaced intervals therealong receives suture material that is braided, woven or otherwise formed therearound, encapsulating the string of pledgets as the suture core.

DESCRIPTION OF THE DRAWINGS

The following drawings illustrate that which is presently regarded as the best mode for carrying out the invention.

FIG. 3 is a side elevation view of a suture of the invention shown as including a series of pledgets or enlarged sections contained therein at spaced intervals; and FIG. 4 is an enlarged sectional view taken within the like 4—4 of FIG. 3 showing a pledget formed onto a string with the suture body formed therearound, encapsulating the pledget and string therein.

DETAILED DESCRIPTION

Figure 1:
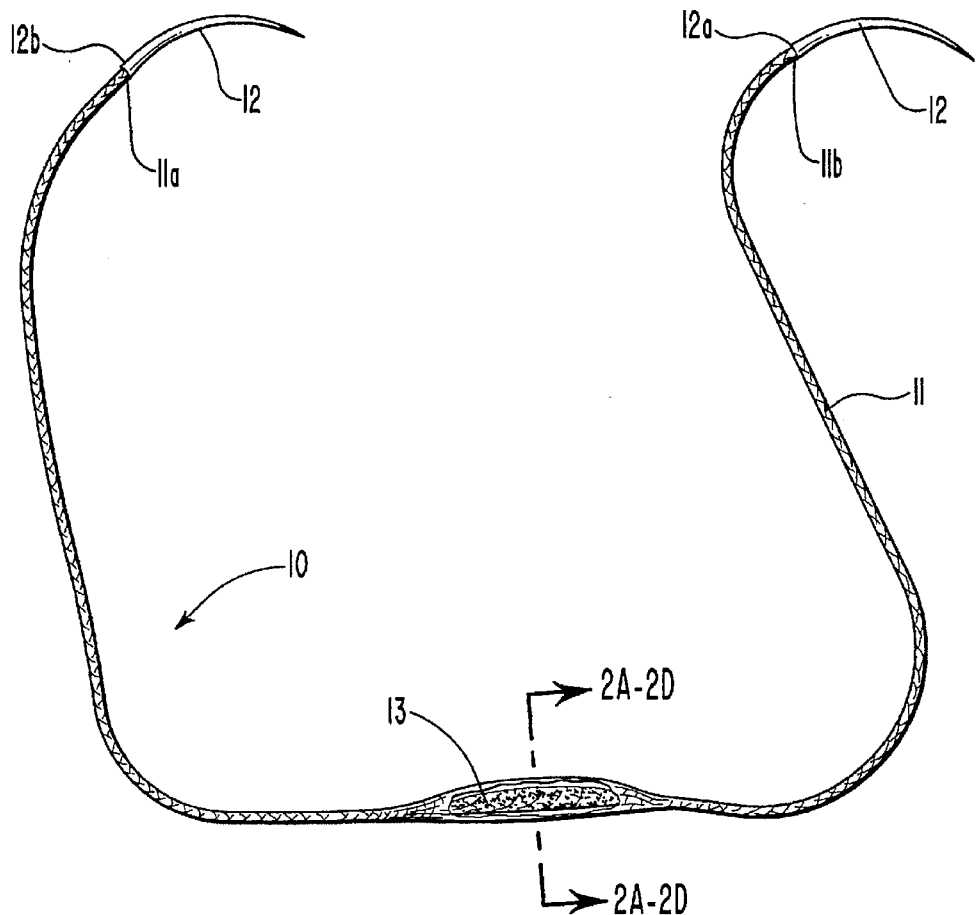
FIG. 1 shows a suture of the invention formed around a single elongate pledget or enlarged section and showing the suture ends connected to ends of a pair of curved needles as are used in medical procedures.
Figure 2A:
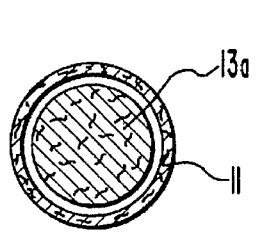
FIG. 2A is a cross sectional view taken along the line 2A-2D—2A-2D of FIG. 1, showing an embodiment of the pledget as having a round cross section.
Figure 2B:
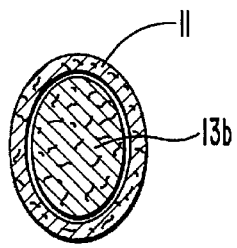
FIG. 2B is a view like that of FIG. 2A only showing the pledget as having an elliptical cross section.
Figure 2C:
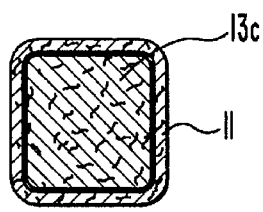
FIG. 2C is another view like that of FIG. 2A only showing the pledget as having a square cross section.
Figure 2D:
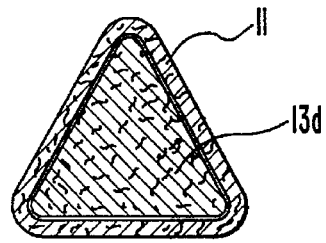
FIG. 2D is still another view like that of FIG. 2A only showing the pledget as having a triangular cross section.

FIG. 1 shows an expandable body suture 10 of the invention as including a suture body 11 that is formed from a conventional suture material by conventional suture forming methods, for example braiding of suture threads along and over a core. Or, alternatively, the suture body and pledget can be formed as a monofilament. Ends 11a and 11b of the suture body 11 are shown connected, as by swaging that involves application of compression thereto, an application of an adhesive thereto, or the like. The suture body and a needle 12 end junction has a greater diameter than that of the suture body. So arranged, needle 12 can be used by a surgeon/operator to form a hole in a bone, ligament, tendon, of the like, and thereafter the suture body 11 is then passed through that formed hole, and the suture body is pulled therethrough. So arranged, the suture body 11 will fit loosely in the formed hole, and when used to connect to an item, as for example, to connect a ligament onto a bone surface, the loose fitting suture body may be movable relative to the hole ends. Such movement could wear the suture body surface and weaken it.

To provide a tight or snug fit of the suture body in the hole formed by one of the needles 12, a pledget 13, enlarged section, or the like, is arranged in the suture body 11, as shown. Shown in FIG. 1, a single pledget 13 is contained within the suture body 11, and in FIG. 3, a pair of spaced pledgets 13 are shown arranged within the suture body 11. Preferably, the combined diameter of the pledget 13 and the suture body 11 wall thickness will be such to provide an enlarged section that will fit snugly in the hole formed by one of the needles 12, taking into account compression of the pledget and suture wall thickness. So arranged, the suture body 11 is pulled through the formed hole to where the pledget 13 is pulled therein, providing a snug fit to restrict suture body movement. Additionally, a tighter fit and larger area will allow for a larger resistive surface area. Further, while pledgets 13 of the same diameter and shape are shown in FIG. 3, it should be understood other size and shapes, such as the shapes of FIGS. 2A through 2D, can be employed within the same suture body 11 within the scope of this disclosure.

Shown in FIGS. 2A through 2D, the pledget 13 can have a round 13a, elliptical 13b, square 13c, triangular 13d, or the like, cross section and is of a diameter to be snugly contained within the suture body 11. Which snug fit can be enhanced by a selection of material from which the pledget 13 is formed. Shown in FIGS. 2A through 2D, the material so used is a cloth or fabric that will provide compression and, accordingly, the cross sectional area of the pledget and suture body 11 can be greater than that of the formed hole, with such compression being anticipated. In practice, the pledget 13 is formed to have a length that is appropriate for the length of a hole, or the like, wherein it will be fitted. Additionally, where the suture body 11 is to be threaded through a plurality of holes, an appropriate number of pledgets 13 of appropriate shapes and sizes can be arranged at spaced intervals in the suture body, as shown in FIG. 3, within the scope of this disclosure.

Where, as shown in FIGS. 2A through 2D, the pledget 13 can be installed in the suture body 11, with the suture formed therearound, the pledget can be maintained onto a cord or string 14, as shown in FIG. 4, with the suture body formed thereover, as by braiding suture strands therealong, to encapsulate both the cord or string 14 and the pledget 13 maintained thereto. The pledget 13, can, as shown in FIG. 4, be formed from a plastic or resinous material and is shaped and attached the cord or string 14 prior to suture strands being woven thereover into the suture body 11. Further, while pledgets 13 are shown as being formed from cloth or fabric in FIGS. 2A through 2D, and from a plastic or resinous material in FIGS. 4, it should be understood that the pledget or pledgets 13 can be formed from any material as it compatible for use in a human body, within the scope of this disclosure, and, as desired may, along with the suture body, be biodegradable.

It should be understood the suture body 11 is preferably manufactured from commonly used materials by conventional methods, such as braiding, or the like, and, in that manufacture, one or more pledgets 13 are included in the suture body, forming the expandable body suture 10 of the invention. Accordingly, although embodiments of the invention have been shown and described herein with reference to the accompanying drawings, it should be understood that the invention is not limited to these embodiments only, and that variations, changes and modifications can be made thereto by one skilled in the art without departing from the scope or spirit of the invention, and a reasonable equivalency thereof.

We claim:

1. An expandable body suture comprising, a suture body formed from conventional suture materials as an envelope to fully contain at least one pledget device that has an elongate body having a greater diameter than the diameter of the suture body adjacent to said pledget and is formed of a biocompatible material; a guide means having a cross sectional diameter that is equal to or slightly less than the diameter of said suture body portion and covered pledget device and is secured to an end of said suture body.

2. An expandable body suture as recited in claim 1, wherein the suture body, in its manufacture, is formed by braiding, or otherwise forming, suture threads over the pledget device that has a substantially round, elliptical, square, rectangular or triangular cross section.

3. An expandable body suture as recited in claim 1, wherein the pledget device is arranged on a cord or string and the suture body is formed over the cord or string and pledget device.

4. An expandable body suture as recited in claim 3, wherein the pledget device is formed from a plastic or resinous material secured onto the cord or string.

5. An expandable body suture as recited in claim 1, wherein the pledget device is formed from a braided cloth or fabric material.

6. An expandable body suture as recited in claim 1, wherein the guide means is at least one needle that is secured at a needle base end onto a suture body end; and the suture body portion covering the pledget device is formed to have a diameter that is slightly greater than said needle to fit snugly into a hole formed by said needle in a bone, ligament, tendon, section of tissue, or the like.

7. An expandable body suture as recited in claim 1, wherein a plurality of pledget devices are maintained at spaced intervals within the suture body.

8. An expandable body suture as recited in claim 1, formed as a monofilament.

9. A method for attaching a suture to a bone utilizing a suture having a body portion that is an envelope fitted over to contain an elongate pledget device with a suture end secured to a guide having a cross sectional diameter that is the same or slightly greater than the suture envelope and pledget device diameter consisting of, forming a hole through a bone or section of tissue to have a diameter that is approximately the diameter of the guide or less; fitting the guide into said bone or tissue hole and pulling said suture through said bone or tissue hole to where the pledget device contained in said suture travels in said bone or tissue hole; and maintaining said pledget device in said bone or tissue hole.

10. A method as recited in claim 9, wherein the guide is a needle and the end of the suture is secured to a blunt end of said needle, with a sharp end of said needle for use in forming the bone or tissue hole.

11. A method as recited in claim 9, wherein a plurality of pledget devices are fitted end to end in the suture body portion.

12. A method as recited in claim 9, wherein the bone or tissue hole is formed to have a slightly smaller diameter than the diameter of the suture body portion containing the pledget device.

* * * * *